United States Patent [19]

Newsome

[11] Patent Number: 5,676,449

[45] Date of Patent: Oct. 14, 1997

[54] HEAD COVERING AND LAMP SYSTEM WITH IMPROVED ADJUSTMENT CAPABILITIES AND INCREASED SAFETY

[76] Inventor: Jeffrey Lee Newsome, 6249 15th St. South, St. Petersburg, Fla. 33705

[21] Appl. No.: 637,555

[22] Filed: Apr. 25, 1996

[51] Int. Cl.⁶ .................................................. F21L 15/14
[52] U.S. Cl. ........................ 362/106; 362/105; 362/287; 362/427; 362/396
[58] Field of Search ........................................ 362/103, 105, 362/106, 190, 191, 196, 231, 202, 287, 285, 396, 418, 427, 288, 382, 184; 2/209.13, 175.1, 906, 175.3

[56] References Cited

U.S. PATENT DOCUMENTS

| | | | |
|---|---|---|---|
| 1,016,730 | 2/1912 | Bartley | 362/106 |
| 1,744,777 | 1/1930 | Lundgren | 362/106 |
| 2,788,439 | 4/1957 | Hesse | 362/106 |
| 4,991,068 | 2/1991 | Mickey | 362/106 |
| 5,485,358 | 1/1996 | Chien | 362/106 |
| 5,567,038 | 10/1996 | Lary | 362/106 |

*Primary Examiner*—Thomas M. Sember

[57] ABSTRACT

A head covering and lamp system comprising a head covering having a central section formed as a strip of fabric with a pocket formed therein. The head covering has a rear section formed with two strips to allow for the positioning on a wearer's head. The head covering also has a relatively stiff forward section constituting a bill extending forwardly for shielding purposes. A lamp has a housing with a forward end and a rearward end including a bulb to project light. A bracket assembly is provided for coupling the lamp to the head covering comprising an interior member formed generally in the shape of a C with upwardly directed free ends and axially aligned cylindrical first members with bearing plates radially disposed teeth. The bracket assembly also includes an exterior member being formed generally in the shape of a U with upwardly directed free ends with axially aligned cylindrical second members rotatably coupled with respect to the first members and the circular bearing plates having radially disposed teeth in mating relationship with the teeth of the interior member. The exterior member also has a hollow tubular member extending downwardly from the lower surface of the exterior member. An electrical assembly initiates and terminates the electrical coupling of electrical power from the batteries to the lamp.

10 Claims, 3 Drawing Sheets

HEAD COVERING AND LAMP SYSTEM WITH IMPROVED ADJUSTMENT CAPABILITIES AND INCREASED SAFETY

BACKGROUND OF INVENTION

1. Field of the Invention

The present invention relates to a head covering and lamp system with improved adjustment capabilities and increased safety and more particularly pertains to adjustably supporting a high intensity lamp over the bill of a visor in a safe manner for illuminating a specific field of vision of a wearer.

2. Description of the Prior Art

The use of caps, visors, helmets and other head coverings with illumination devices thereon to provide illumination for a wearer is known in the prior art. More specifically, head coverings with illumination devices thereon heretofore devised and utilized for the purpose of providing illumination are known to consist basically of familiar, expected, and obvious structural configurations, notwithstanding the myriad of designs encompassed by the crowded prior art which has been developed for the fulfillment of countless objectives and requirements.

By was of example, U.S. Pat. No. 539,192 to Rodrigues et al discloses an electric light head gear for personal wear.

U.S. Pat. No. 897,588 to Cogswell et al discloses a miner's cap and lamp.

U.S. Pat. No. 1,146,979 to Walters et al discloses a trouble lamp.

U.S. Pat. No. 1,532,206 to Snow discloses a socket for electric lamps.

U.S. Pat. No. 1,559,451 to Parker discloses a fireman's helmet lamp combination.

U.S. Pat. No. 1,744,777 to Lundgren discloses a cap supported lamp.

U.S. Pat. No. 2,421,643 to Ostli discloses a safety helmet.

U.S. Pat. No. 2,448,240 to Walwort discloses an electric lamp attachment for caps.

U.S. Pat. No. 2,524,881 to Chambers discloses a combined clasp and lighting implement.

U.S. Pat. No. 3,133,705 to Eickelman discloses a head lamp carrier and adjuster.

U.S. Pat. No. 4,406,040 to Cannone discloses illumination devices.

U.S. Pat. No. 4,473,869 to De Widt discloses a luminaire with resilient sleeve and band connection.

U.S. Pat. No. 4,593,683 to Blaha discloses a medical examination instrument with headband support.

Lastly, U.S. Pat. No. 4,991,068 to Mickey discloses a lamp attachment for a hat. The Mickey device, however, includes loose electrical wires while the pivoting mechanism provide no positive locking of the lamp in a preset orientation.

In this respect, the head covering and lamp system with improved adjustment capabilities and increased safety according to the present invention substantially departs from the conventional concepts and designs of the prior art, and in doing so provides an apparatus primarily developed for the purpose of adjustably supporting a high intensity lamp over the bill of a visor in a safe manner for illuminating a specific field of vision of a wearer.

Therefore, it can be appreciated that there exists a continuing need for a new and improved head covering and lamp system with improved adjustment capabilities and increased safety which can be used for supporting a high intensity lamp over the bill of a visor in a safe manner for illuminating a specific field of vision of a wearer. In this regard, the present invention substantially fulfills this need.

SUMMARY OF THE INVENTIONS

In view of the foregoing disadvantages inherent in the known types of head coverings with illumination devices thereon for providing illuminating to a wearer now present in the prior art, the present invention provides an improved head covering and lamp system with improved adjustment capabilities and increased safety. As such, the general purpose of the present invention, which will be described subsequently in greater detail, is to adjustably support a high intensity lamp over the bill of a head covering in a safe manner for illuminating a specific field of vision of a wearer and the associated method which has all the advantages of the prior art and none of the disadvantages.

To attain this, the present invention essentially comprises a new and improved head covering and lamp system with improved adjustment capabilities and increased safety comprising, in combination, a visor having a central section formed as a strip of fabric with an upper edge and a pocket formed therein, the pocket adapted to be opened and closed and sealed along the upper edge with a pile-type fastener, the visor having a rear section formed with two strips, each strip having a forward end coupled to the central section, each strip having a free rearward end with a piece of pile-type fastener to allow for the adjustable coupling thereof around the back of the head of the wearer, the visor also having a relatively stiff forward section constituting a bill extending forwardly to a location above the eyes of a wearer for shielding purposes; a lamp having a tubular housing with a forward end and a rearward end, the forward end including a lens with a high intensity bulb thereadjacent with the housing to project light through the lens in a forward direction therefrom; a bracket assembly for coupling the lamp to the visor comprising an interior member attached to a central section of the wall of the housing, the interior member being formed in the shape of a C with upwardly directed free ends, the free ends having axially aligned cylindrical projections on opposite sides of the lamp housing with circular bearing plates radially disposed teeth facing outwardly from its exterior surfaces, the bracket assembly also including an exterior member being formed in the shape of a U of a resilient relatively rigid plastic with upwardly directed free ends positioned exteriorly of the upwardly directed free ends of the interior member and with axially aligned cylindrical recesses rotatably supporting the projections of the interior member with circular bearing plates having radially disposed teeth facing inwardly from its interior surfaces in mating relationship with the teeth of the interior member, the exterior member also having a hollow tubular member or a rigid plastic extending downwardly from the lower surface of the exterior member and secured at its lower end to the bill for holding the lamp at a forward elevated location with respect to the visor; and an electrical assembly having a pair of battery cases removably secured within the pocket of the visor adjacent to the opposite side thereof, the battery cases adapted to removably receive batteries and with electrical lines coupled to the batteries and extending forwardly through the visor pocket and through the tubular member to the lamp, the wiring also including a button secured to the right side of the visor and extending upwardly thereof, the button including an elastomeric resilient shield the button with electrical lines coupled to the lines emanating from one of the batteries to initiate and terminate the electrical coupling of the electrical power from the batteries to the lamp.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent of legal terms or phraseology, to determine quickly from a cursory inspection the nature and essence of the technical disclosure of the application. The abstract is neither intended to define the invention of the application, which is measured by the claims, nor is it to be limiting as to the scope of the invention in any way.

It is therefore an object of the present invention to provide anew and improved head covering and lamp system with improved adjustment capabilities and increased safety which has all the advantages of the prior art caps with lights thereon for providing illumination to a wearer and none of the disadvantages.

It is another object of the present invention to provide a new and improved head covering and lamp system with improved adjustment capabilities and increased safety which may be easily and efficiently manufactured and marketed.

It is a further object of the present invention to provide a new and improved head covering and lamp system with improved adjustment capabilities and increased safety which is of durable and reliable constructions.

An even further object of the present invention is to provide a new and improved head covering and lamp system with improved adjustment capabilities and increased safety which is susceptible of a low cost of manufacture with regard to both materials and labor, and which accordingly is then susceptible of low prices of sale to the consuming public, thereby making such head covering and lamp system with improved adjustment capabilities and increased safety economically available to the buying public.

Still yet another object of the present invention is to provide a new and improved head covering and lamp system with improved adjustment capabilities and increased safety which provides in the apparatuses and methods of the prior art some of the advantages thereof, while simultaneously overcoming some of the disadvantages normally associated therewith.

Still another object of the present invention is to adjustably support, in a positive and secure manner, a high intensity lamp over the ill of a head covering in a safe manner for illuminating a specific field of vision of a wearer.

Even still another object of the invention is to support a high intensity lamp over the bill of a cap with safe electrical components.

Lastly, it is an object of the present invention to provide a new and improved head covering and lamp system comprising a head covering having a central section formed as a strip of fabric with a pocket formed therein, the head covering having a rear section formed with two strips to allow for the positioning on a wearer's head, the head covering also having a relatively stiff forward section constituting a bill extending forwardly for shielding purposes; a lamp having a housing with a forward end and a rearward end including a bulb to project light; a bracket assembly for coupling the lmap to the head covering comprising an interior member attached to the housing, the interior member being formed generally in the shape of a C with upwardly directed free ends, the free ends having axially aligned cylindrical first members on opposite sides of the housing with bearing plates radially disposed teeth, the bracket assembly also including an exterior member being formed generally in the shape of a U of a resilient material with upwardly directed free ends positioned exteriorly of the upwardly directed free ends of the interior member and with axially aligned cylindrical second members rotatably coupled with respect to the first members and with circular bearing plates having radially disposed teeth in a mating relationship with the teeth of the interior member, the exterior member also having a hollow tubular member extending downwardly from the lower surface of the exterior member and secured at its lower end to the head covering for holding the lamp; and an electrical assembly having a battery support secured within the pocket of the head covering, the battery support adapted to removably receive batteries and with electrical lines coupled to the batteries and extending through the head covering pocket and through the tubular member to the lamp, the wiring also including a button secured to the head covering to initiate and terminate the electrical coupling of the electrical power from the batteries to the lamp.

These together with other objects of the invention, along with the various features of novelty which characterize the invention, are pointed out with particularity in the claims annexed to and forming a part of this disclosure. For a better understanding of the invention, its operating advantages and the specific objects attained by its use, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given tot he following detailed description thereof. Such description makes reference to the annexed drawings wherein.

The same reference numerals refer to the same parts through the various Figures.

DESCRIPTION OF THE PREFERRED EMBODIMENT

Figure 1:
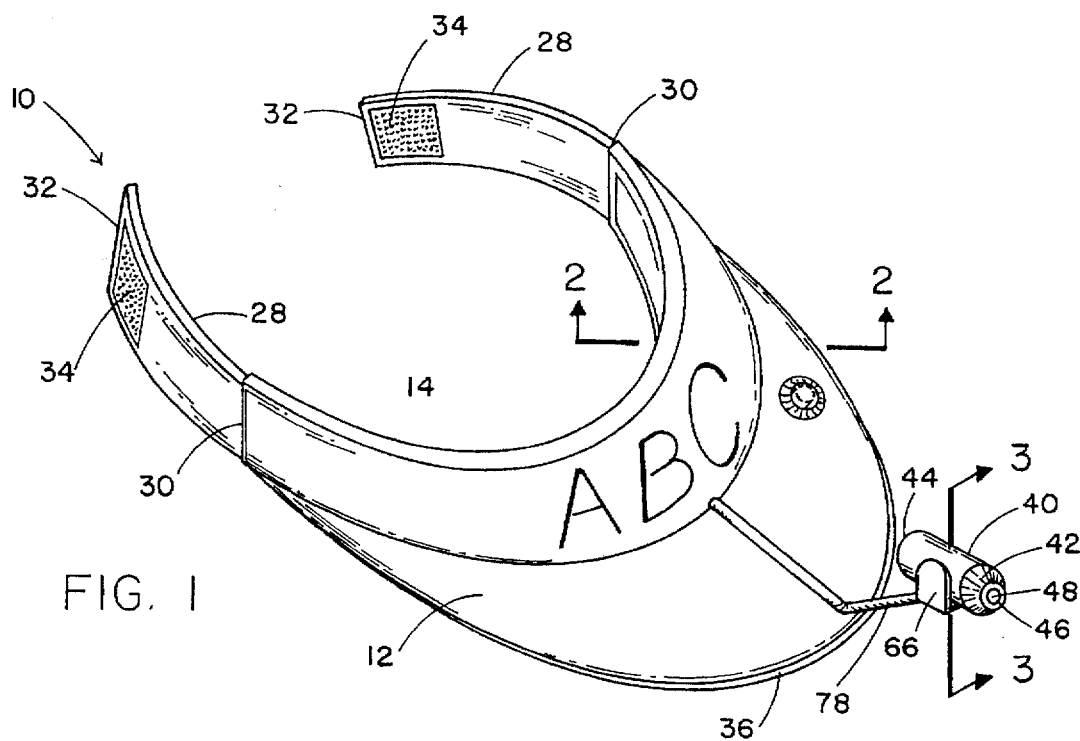
FIG. 1 is a perspective illustration of the preferred embodiment of the head covering and lamp system with improved adjustment capabilities and increased safety constructed in accordance with the principles of the present invention.
Figure 2:
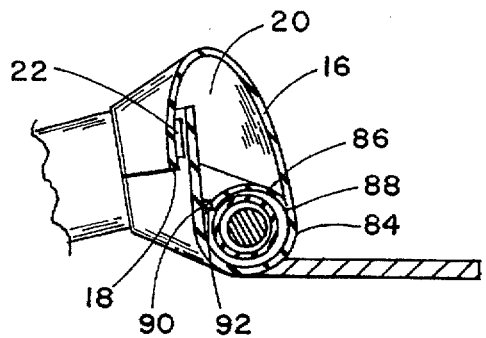
FIG. 2 is a cross section view taken along line 2—2 of FIG. 1.
Figure 3:
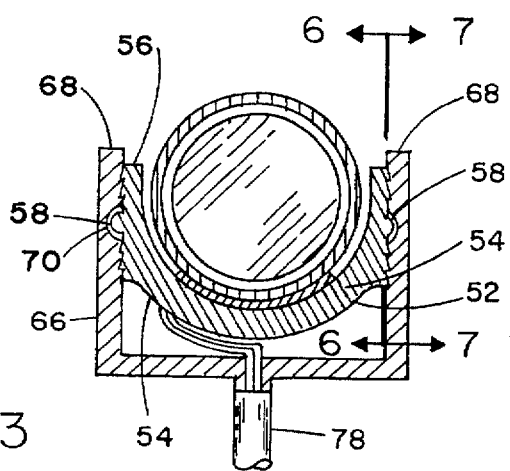
FIG. 3 is a cross section view of the system shown in FIG. 1.
Figure 4:
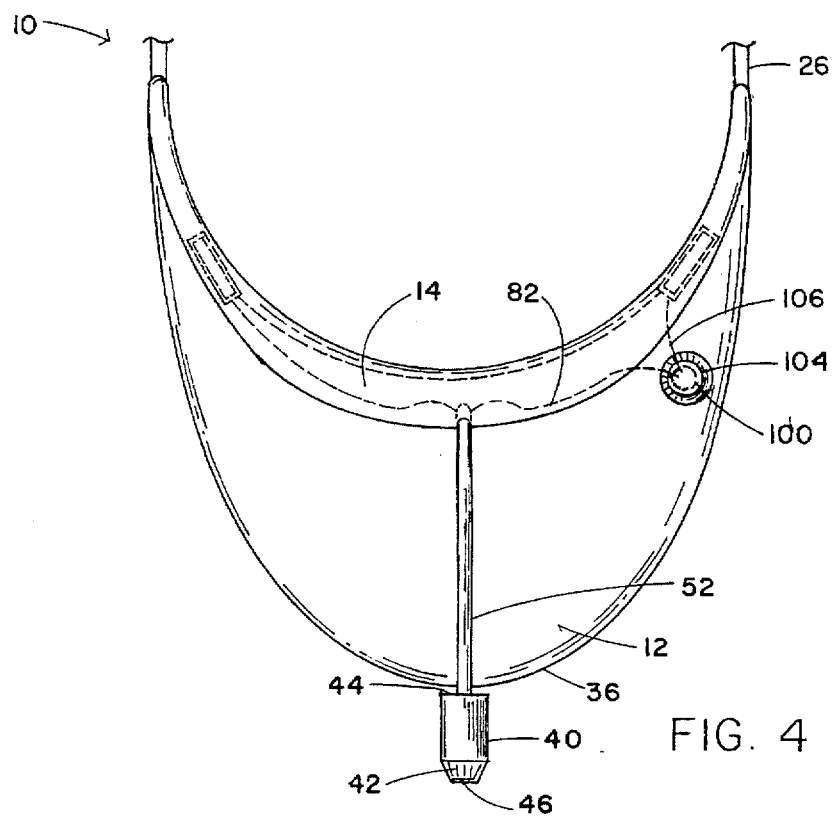
FIG. 4 is a top elevational view of the system shown in FIG. 1.
Figure 5:
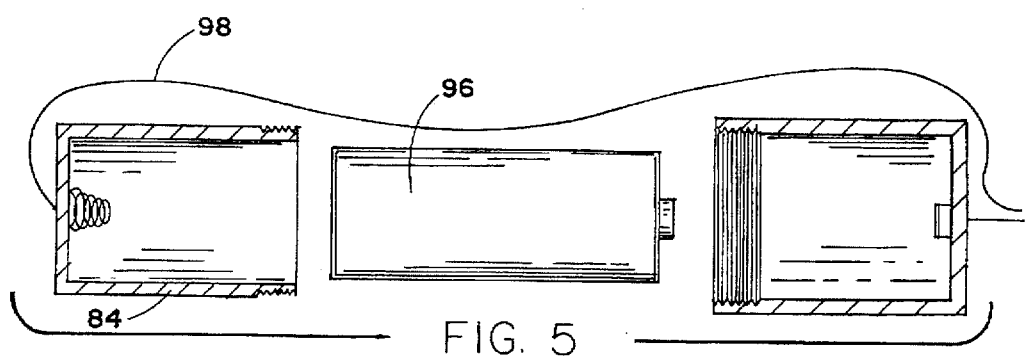
FIG. 5 is an exploded elevational view of the battery case shown in FIG. 4.
Figure 6:
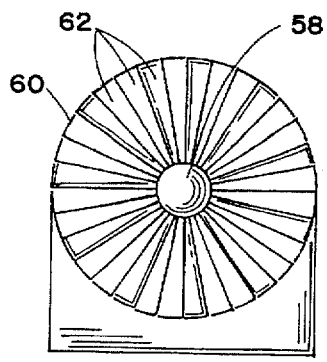
FIG. 6 is a front elevational view of the one of the facing plates taken along line 6—6 of FIG. 3.

With reference now to the drawings, and in particular to FIG. 1 thereof, the preferred embodiment of the new and improved head covering and lamp system with improved adjustment capabilities and increased safety embodying the principles and concepts of the present invention and generally designated by the reference numeral 10 will be described.

The present invention, the new and improved head covering and lamp system with improved adjustment capabilities and increased safety is comprised of a plurality of components. Such components are individually configured and correlated with respect to each other so as to attain the desired objective.

The central component of the system 10 of the present invention is a visor 12. The visor has a central section 14. The central section if formed as a strip of fabric 16 having an edge 18 adjacent to its upper extent with a pocket 20 formed therein. The pocket is adapted to be opened and closed by sealing along the edge 18 with a pile-type fastener 22. The opening of the pocket has its opened edge facing downwardly to abate the possibility of rain, water, or other debris from entering the pocket. The front of the central section may be provided with indicia such as a team logo, an advertising message or any appropriate writing, picture, symbol or the like.

The visor also has a rear section 26. The rear section is formed with two strips 28. Each strip has a forward end 30 coupled to the central section. Each strip also has a free rearward end 32. A piece of pile-type fastener 34 is secured thereto. This allows for the adjustable coupling of the strips and that around the back of the head of a wearer. The visor also has a relatively stiff forward section 36. The forward section constitutes a bill extending forwardly of the wearer to a location above the eyes. This is for the purpose of shielding the eyes of a wearer as from the sun.

The next component of the system 10 is a lamp 38. The lamp has a tubular housing 40. It is formed with a forward end 42 and a rearward end 44. The forward end includes a lens 46. The housing also has a high-intensity bulb 48 within the housing adjacent to the lens. The function of the bulb is to project light through the lens in a forward direction.

Next provided is a bracket assembly 52. The bracket assembly functions for coupling the lamp to the visor. The bracket assembly comprises an interior member 54. The interior member is attached to a central section of the wall of the housing. Securement is by an adhesive or the like. The interior member is formed in the shape of a C. It has upwardly directed free ends 56. The free ends have axially aligned cylindrical projections 58. Such projections are located on opposite sides of the lamp housing. Also on opposite sides of the lamp housing is a circular bearing plates 60. Such plates have radially disposed teeth 62. Such teeth face outwardly from the exterior free surfaces of the plates.

The bracket assembly also includes an exterior member 66. The exterior member is formed in the shape of a U. It is formed of a resilient, relatively plastic material. It has upwardly directed free ends 68. Such free ends are positioned exteriorly of the upwardly directed free ends of the interior member. The exterior member is formed with axially aligned cylindrical recesses 70 in the center thereof. Such recesses are for rotatably supporting the projections of the interior member. In addition, circular bearing plates 72 are on each face of the exterior member. The bearing plates have radially disposed teeth 74 facing inwardly from its interior surface. Such teeth are adapted to be located in mating relationship with the teeth of the interior member.

The exterior member also has a hollow tubular member 78. Such tubular member is fabricated of a rigid plastic material. It extends downwardly from the lower surface of the exterior member. It is secured at its lower end to the bill. The tubular member functions for holding the lamp at a forward elevated location with respect to the visor.

The last component of the system 10 is an electrical assembly 82. Such electrical assembly has a pair of battery cases 84. Such battery cases are removably secured within the pocket of the visor adjacent to the opposite sides thereof. A strap 86 secures each battery case in position to preclude inadvertent movement thereof. The straps each have a secured end 88 stitched within the pocket and a free end 90. The free end is provided with a pile-type fastener 92 for coupling with a pile-type fastener within the pocket to effect the removable securement therebetween and the capability of removing the battery case from the pocket when needed. The battery cases are adapted to be removably received batteries 96 therein for constituting a power source for the system. The preferred batteries are of the AA size although other types could be used. In association therewith, electrical lines 98 are coupled between the batteries and extend forwardly though the visor pocket and through the tubular member to the lamp. The wiring also includes a button 100 preferably secured to the right side of the visor. It should be understood, however, that the button could readily be placed on the left side to suit the desires of a wearer.

The button 100 includes an elastomeric resilient shield 104 encasing the button to preclude moisture from entering to the button and its electrical components. The button, with its electrical lines 106 coupled to the lines emanating from the battery to the lamp, function to initiate and terminate the operation of the system 10. Such is done by the initiating and terminating of the electrical coupling of the power from the batteries to the lamp to the button. The button is preferably of a conventional design whereby one press of the button followed by its release will switch its state. If off, the pressing and release will turn on the lamp. If on, the pressing and release will turn the lamp off.

Figure 8:
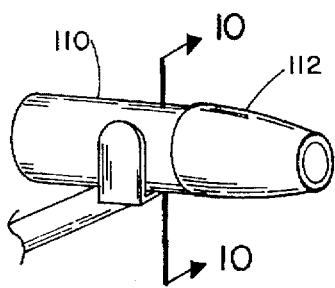
FIG. 8 is a perspective illustration of the front portion of the lamp constructed in accordance with an alternate embodiment of the invention.
Figure 10:
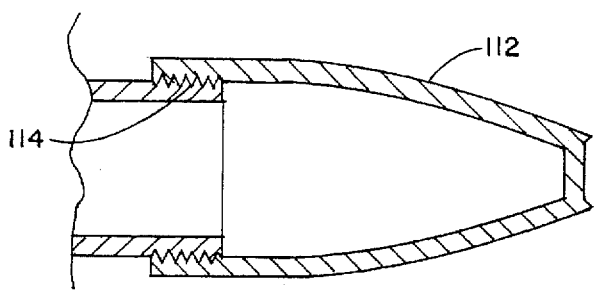
FIG. 10 is a cross sectional view taken along line 10—10 of FIG. 8.
Figure 11:
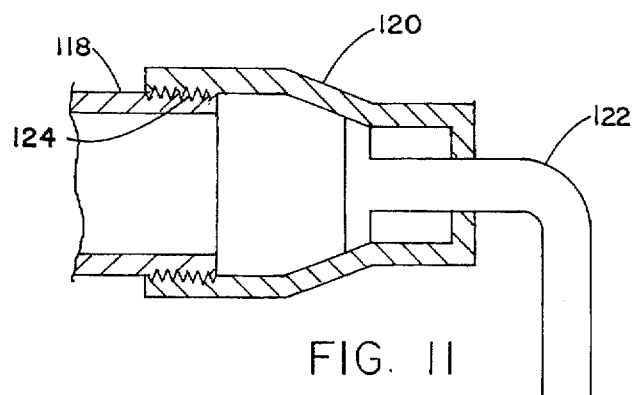
FIG. 11 is a cross sectional view taken along line 11—11 of FIG. 9.

The embodiment of FIG. 8 illustrates a lamp 110 having a detachable forward end 112. Cooperable screw threads 114 allow for the coupling and release of the end 112 from the remainder of the lamp. In this embodiment, the removable member is fabricated of a transparent colored material. The preferred material is red for providing a limited light but yet sufficient light so as to allow the user to be seen by others. The removable member may be separated from the remainder of the lamp and replaced by an other removable member of a different color to suit any particular purpose. Note FIG. 10 for a cross sectional illustration of this embodiment.

Figure 9:
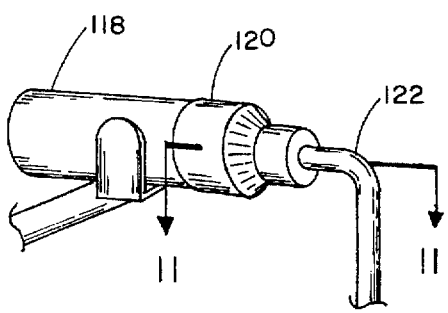
FIG. 9 is a perspective illustration of the front portion of the lamp constructed in accordance with yet another alternate embodiment of the invention.

The embodiment of FIG. 9 discloses another lamp 118 with an other type of removable member 120 formed with a transparent light pipe 122. The light pipe 122 is fitted within an aperture at the forward end of its supporting attachment 120. Screw threads 124 allow for the adjustable coupling of the removable member 120 and its light pipe 122 with respect to the remainder of the lamp 118. The use of the transparent light pipe of a plastic material allows for the user to direct light from the lamp in any direction for any particular purpose. A preferred purpose is for reading wherein the light pipe 122 may be directed downwardly toward the material to be read.

Figure 12:
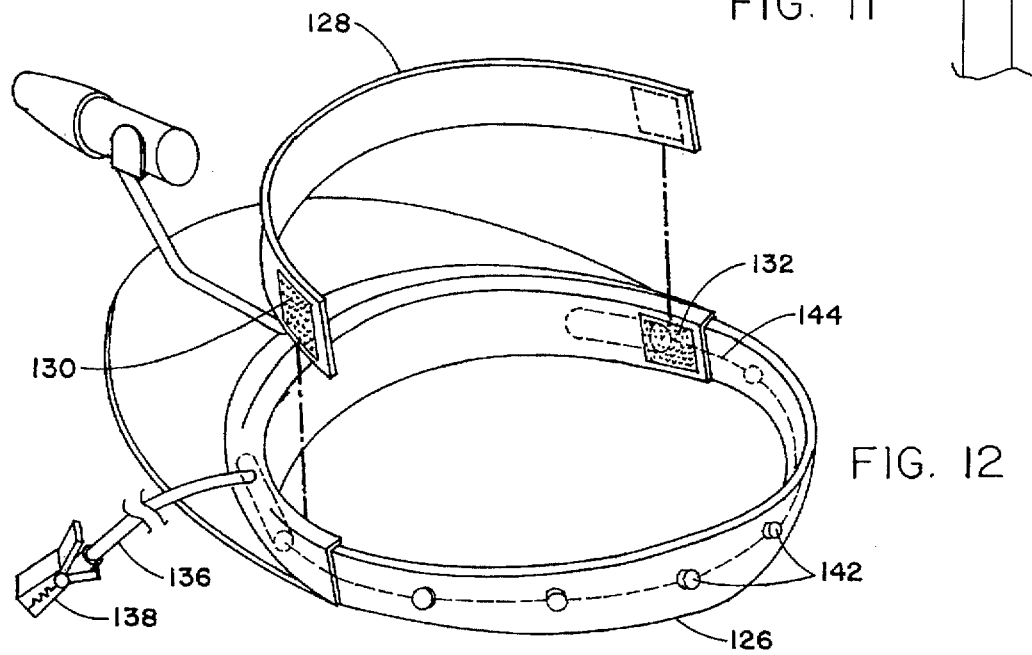
FIG. 12 is an exposed perspective illustration of a yet further alternate embodiment of the invention.

The final embodiment of the invention is shown in FIG. 12. In this embodiment, the hat is formed with its rearward band 126 configured to be a close loop around the head of the wearer. If desired, such band could be made of an elastic material to fit any of a plurality of wearers with different size heads. In the alternative, it could be of an inextensive material with elastic inserts at a spaced point or points, as for example, adjacent to the temples of a wearers.

Such alternate embodiment of FIG. 12 also features a removable sweat band 128. Such sweat band is formed only in the forward region of the hat opening to contact the brow of the wearer. It has patches of a pile-type fastener 130 secured to its ends on its exterior faces. Such pile-type fasteners are adapted to cooperably join with similar patches of pile-type fasteners 132 formed in exposed surfaces of the band adjacent to the temples of a wearer. The sweat band 128 is adapted to absorb the perspiration of the user while allowing removal of the sweat band for cleansing purposes.

One additional feature of the FIG. 12 embodiment, is the use of a bungee cord 136, preferably of an elastic material. Such cord is formed with a clip 138 at each end. One clip is adapted to be secured to the hat at any location in accordance with the desires of the user. The other end is adapted to be coupled to an other portion of apparel of the user of the hat. In this manner, if the hat were to be inadvertently removed as by being blown off the wearer, the cap would not be lost since it would still be attached to the wearer through the cord 135.

Figure 7:
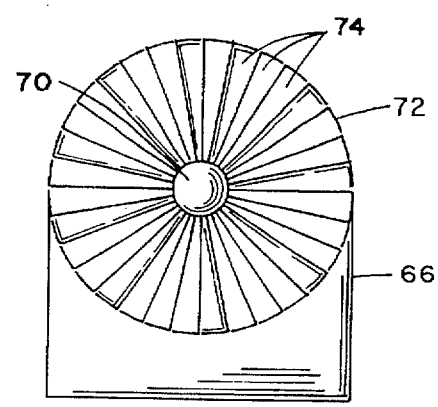
FIG. 7 is a front elevational view of the other of the facing plates taken along line 7—7 of FIG. 3.

The final feature of the FIG. 12 embodiment is a plurality of lights 142. such lights are at spaced locations across the rear of the hat. They are exposed for view by third parties. Ann electrical wire 144 couples the light to the battery and switch as in the primary embodiment of FIGS. 1 and 7. In this embodiment, when the switch is turned on to illuminate the lamp, the lights 142 are similarly illuminated for allowing the use to be seen by third parties. This provides an additional element of safety to the system 10 of the present invention.

As to the manner of usage and operation of the present invention, the same should be apparent from the above description. Accordingly, no further discussion relating to the manner of usage and operation will be provided.

With respect to the above description then, it is to be realized that the optimum dimensional relationships for the part of the invention, to including variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. A new and improved head covering and lamp system with improved adjustment capabilities and increased safety comprising, in combination:

a visor having a central section formed as a strip of fabric with an upper edge and a pocket formed therein, the pocket adapted to be opened and closed and sealed along the upper edge with a pile-type fastener, the visor having a rear section formed with two strips, each strip having a forward end coupled to the central section, each strip having a free rearward end with a piece of pile-type fastener to form an adjustable coupling adapted to be positioned at a location around a back of a head of a wearer, the visor also having a relatively stiff forward section constituting a bill extending forwardly from said central section to a location above the eyes of a wearer for shielding purposes;

a lamp having a tubular housing with a forward end and a rearward end, the forward end including a lens with a high intensity bulb adjacent to the lens within the housing to project light through the lens in a forward direction therefrom;

a bracket assembly for coupling the lamp to the visor comprising an interior member attached to a central section of the housing, the interior member being formed in a C-shaped configuration with upwardly directed free ends, the free ends having axially aligned cylindrical projections on opposite sides of the lamp housing with circular bearing plates formed with exterior surfaces and having radially disposed teeth facing outwardly from the exterior surfaces, the bracket assembly also including an exterior member being formed in of a resilient relatively rigid plastic with upwardly directed free ends positioned exteriorly of the upwardly directed free ends of the interior member and with axially aligned cylindrical recesses rotatably supporting the projections of the interior member with circular bearing plates formed with exterior surfaces and having radially disposed teeth facing inwardly from the interior surfaces of said external member in mating relationship with the teeth of the interior member, the exterior member also having a hollow tubular member of a rigid plastic with an upper and a lower end and extending downwardly from the exterior member and secured at its lower end to the bill for holding the lamp at a forward elevated location with respect to the visor; and an electrical assembly having a pair of battery cases removably secured within opposite sides of the pocket of the visor, the battery cases adapted to removably receive batteries and having electrical lines coupled to the batteries and extending forwardly through the visor pocket and through the tubular member to the lamp, the lines also including a button secured to a right side of the visor and extending upwardly thereof, the button and the electrical lines being coupled to the lines emanating from one of the batteries to initiate and terminate electrical power from the batteries to the lamp.

2. A head covering and lamp system comprising:

a head covering having a central section formed as a strip of fabric with a pocket formed therein, the head covering having a rear section coupled to the central section to allow for the positioning on a wearer's head, the head covering also having a relatively stiff section forwardly from said central section constituting a bill extending forwardly for shielding purposes;

a lamp having a housing with a forward end and a rearward end including a bulb to project light;

a bracket assembly for coupling the lamp to the head covering comprising an interior member attached to the housing, the interior member being formed generally in a C-shaped configuration with upwardly directed free ends, the free ends having axially aligned cylindrical first members on opposite sides of the housing with bearing plates having radially disposed teeth, the bracket assembly also including an exterior member being formed generally in a U-shaped configuration of a resilient material with upwardly directed free ends positioned exteriorly of the upwardly directed free ends of the interior member and with axially aligned cylindrical second members rotatably coupled with respect to the first members and with circular bearing plates having radially disposed teeth in mating relationship with the teeth of the interior member, the exterior member also having a hollow tubular member extending downwardly on a lower surface of the exterior member and secured at a lower end to the head covering for holding the lamp; and an electrical assembly having a battery support secured within the pocket of the head covering, the battery support adapted to removably receive batteries and having electrical lines coupled to the batteries and extending through the head covering pocket and through the tubular member to the lamp, the wiring also including a button secured to the head covering to initiate and terminate the electrical power from the batteries to the lamp.

3. The device as set forth in claim 2 and further including separable straps to releasably couple the battery supports within the pocket.

4. The device as set forth in claim 2 wherein the button has normally separable electrical contacts and is located within an elastomeric shield.

5. The device as set forth in claim 2 wherein the bracket assembly is fabricated of plastic.

6. The device as set forth in claim 2 and further including a removable member located at the leading edge of the lamp for allowing illumination of one of a plurality of colors.

7. The device as set forth in claim 2 and further including a removable device with a light pipe positioned at the leading edge of the lamp for directing light in one particular direction at the discretion of the user.

8. The device as set forth in claim 2 and further including a sweat band positioned within the cap and adapted to be located over the brow of wearer with coupling means to allow attachment and removal of the band with respect to the cap.

9. The device as set forth in claim 2 and further including a bungee cord with a clip at its opposite ends, one of the clips adapted to be coupled to the head covering and the other end adapted to be coupled to an other item of apparel of the wearer of the head covering.

10. The device as set forth in claim 2 and further including a plurality of small lights positioned across the rear section of the head covering adapted to be turned on and off with a switch.

* * * * *